US008642286B2

(12) United States Patent
Lin et al.

(10) Patent No.: US 8,642,286 B2
(45) Date of Patent: Feb. 4, 2014

(54) METHODS FOR IDENTIFYING NEURIPOTENT CELLS

(76) Inventors: Chih-Min Lin, San Diego, CA (US); Alexander Kharazi, San Diego, CA (US)

(*) Notice: Subject to any disclaimer, the term of this patent is extended or adjusted under 35 U.S.C. 154(b) by 97 days.

(21) Appl. No.: 12/061,967

(22) Filed: Apr. 3, 2008

(65) Prior Publication Data

US 2009/0253591 A1 Oct. 8, 2009

(51) Int. Cl.
*C12Q 1/02* (2006.01)
*C40B 50/06* (2006.01)

(52) U.S. Cl.
USPC ............................................... 435/29; 506/26

(58) Field of Classification Search
USPC ............................................... 435/29; 506/26
See application file for complete search history.

(56) References Cited

U.S. PATENT DOCUMENTS

2008/0254004 A1* 10/2008 Terskikh et al. ............ 424/93.7

OTHER PUBLICATIONS

Lee et al. Directed Differentiation and Transplantation of Human Embryonic Stem Cell-Derived Motoneurons; Stem Cells, vol. 25 (2007) pp. 1931-1939.*

Goldstein et al. Integration and Differentiation of Human Embryonic Stem Cells Transplanted to the Chick Embryo; Developmental Dynamics, vol. 225 (2002) pp. 80-86.*

Beauvais-Jouneau et al. A Novel Model to Study the Dorsolateral Migration of Melanoblasts; Mechanisms of Development, vol. 89 (1999) pp. 3-14.*

Sigurjonsson et al. Adult Human Hematopoietic Stem Cells Produce Neurons Efficiently in the Regenerating Chicken Embryo Spinal Cord; Proceedings of the National Academy of Science, vol. 102, No. 14 (2005) pp. 5227-5232.*

Gilbert et al. Tissue Architecture of the Central Nervous System; Developmental Biology, 6th Ed. (2000), downloaded from http://ncbi.nlm.gov/books/NBK10047/.*

Levitt et al. Coexistence of Neuronal and Glial Precursor Cells in Cerebral Ventricular Zone OS the Fetal Monkey: An Ultrastructural Immunoperoxidase Analysis; The Journal of Neuroscience, vol. 1, No. 1 (1981) pp. 27-39.*

* cited by examiner

*Primary Examiner* — Jon P Weber
*Assistant Examiner* — Paul Martin
(74) *Attorney, Agent, or Firm* — Timothy M. Brown, Esq.

(57) ABSTRACT

The invention is a method for using an avian embryo to identify the neuripotency of a cell population. The invention may be used for applications such as screening for candidate neuripotent cell lines for masterbanking, validation of working cell banks, and identifying agents and conditions capable of inducing neural differentiation in a cell population.

39 Claims, 6 Drawing Sheets

METHODS FOR IDENTIFYING NEURIPOTENT CELLS

FIELD OF THE INVENTION

The invention relates to the field of cell biology. In particular, the invention relates to an in vivo model for identifying neuripotent stem cells and neuripotent progenitor cells.

BACKGROUND

Animal models are essential in the development of preventive, diagnostic and therapeutic procedures for diseases in a wide spectrum of fields including neural stem cell (NSC) research. To elicit or identify the potency of stem cells in animal models is a critical procedure in the development of further applications. Chicken and mammalian brains share similar activities and mechanisms of migration pattern and differentiation during development (Alvarez-Buylla and Nottebohm, 1988; Aroca et al. 2006).

NSCs have been demonstrated to reside in the sub ventricular zone (SVZ) of the lateral ventricle and the dentate gyrus subgranular zone (SGZ) of the hippocampus in rodent (Lim et al. 2007). Neural stem cells (NSCs) are self-renewing and generating neuronal and glial cells in nervous system. Therefore, transplantation of neural stem cells (NSCs) has been proposed as therapy for a wide range of central nervous system disorders, including neurodegenerative diseases (e.g., Parkinson's disease), demyelinating disorders (e.g., multiple sclerosis), stroke, and trauma. Although there is great hope for the success of such therapies, the clinical development of NSC-based therapies is still in its infancy.

To establish the optimal cell preparation procedures, assays are needed to evaluate the potency of NSCs, i.e., their ability to perform stem cell functions after injection into a patient, thereby effecting tissue repair. Ideally, it would be desirable to have a system that would allow assessing the stem cells' potency in a reliable way for every stem cell manufacturing protocol.

To understand the potency of NSCs and stimulated NSCs is the greatest challenge in the development of replacement therapies. Although significant advances in this field have been made over the past decade, no cost effective and accessible assay is currently available. Expression marker profiles have been used with some success to identify stem cells capable of assuming a neural phenotype. However, these profiles do not often provide a good indication of stem cell potency in an in vivo environment.

Embryonic mouse models have been used in some capacity for measuring the potency of NSC in vivo (Proc Natl Acad Sci USA. Dec. 20, 2005; 102(51): 18644-8). However, these models are expensive to maintain and their isolation in utero and small size makes them difficult to work with. The gestation period for mice also places a time constraint on this model. What is needed in the art therefore is a quick, inexpensive and easily accessible in vivo model for the measurement of NSC potency.

SUMMARY OF THE INVENTION

Accordingly, the present invention provides an efficient assay for evaluating the potency of NSC in an in vivo environment. The assay is based on the capacity of the donor NSCs to migrate inside the chicken embryo brain host. The Example below discloses the transplanting of either immature (i.e. undifferentiated) or differentiated NSCs into the ventricle of chicken embryo forebrain at stage 26 (embryonic day 5).

The inventors found that human donor, undifferentiated NSCs upon injection (transplantation) into the chick brain penetrated further into the brain tissue, migrated, survived, differentiated and integrated into the chick brain; in contrast, differentiated, donor NSCs did not.

The present invention demonstrates that an assay of the potency of neural stem cells using a chicken embryo model is a time and cost-effective system for screening the potency of neural stem cells in vivo.

In this study, either undifferentiated NSCs or differentiated neuronal, cells were transplanted into the ventricle of the chicken embryo forebrain at stage 26 (embryonic day 5). The data showed that NSCs migrated, and engrafted into the chicken brain in a time dependent manner (day 4 and day 6 post-transplantation). However, only a small number of differentiated neuronal cells migrated and engrafted. Most of the differentiated cells remained on the long side of the ventricle area in the chicken embryo brain. The advantage of the chicken embryo model is that it only takes 11 days to verify the potency of NSCs with no requirement of an animal facility while a conventional mouse model requires an animal facility and around 2 months to complete.

The time and expense benefits of the inventors' chick embryo assay lends itself to a number of applications. These include (a) the validation of master cell banks, (b) the identification of priming and activation agents (and combinations thereof), (c) the identification of neuripotent NSC for transplantation studies and transplantation therapies, and (d) the identification of the optimal number of in vitro cell, culture passages for neuripotency of a cell population.

BRIEF DESCRIPTION OF THE DRAWINGS

FIG. 2 shows that undifferentiated human neural stem cells migrated in chicken embryo brain after transplantation.

DEFINITIONS

Figure 1:
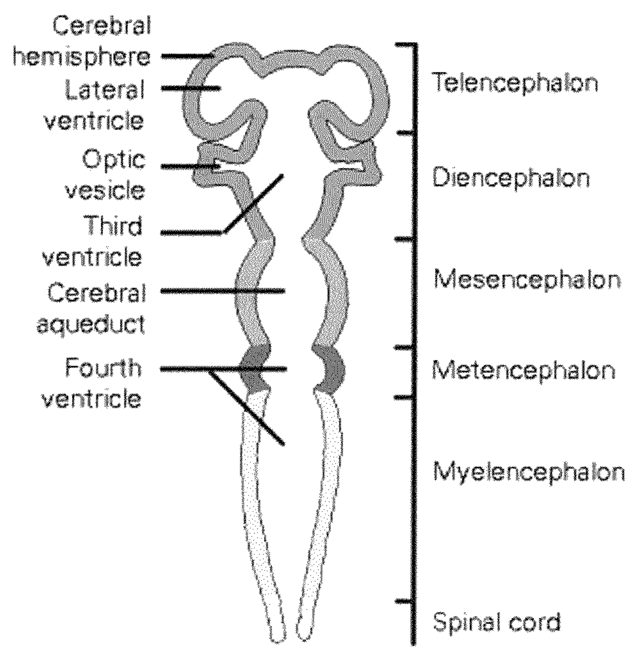
FIG. 1 depicts the central nervous tissue of an avian embryo in the ventricle stage.

"Stem cell" refers to a cell which has the ability to both self-renew and undergo differentiation to form one or more specialized cell types. Stem cells have varying degrees of potency. Potency specifies the differentiation potential (i.e. the ability to differentiate into different cell types) of the stem cell. A precursor cell is one non-limiting example of a stem cell.

The terms "progenitor," "progenitor cell," "precursor cell" and "precursor" as used herein refer to a partially differentiated stem cell that is committed to a specific developmental pathway, i.e. lineage. Precursor cells have limited, proliferative ability and limited potency. One non-limiting example of a precursor cells is a "neural precursor," which is dedicated to the development of a neural cell such as, for example, a neuron, an astrocyte, or an oligodendrocyte.

"Multi potent," or "multipotency," refers to the ability of a stern cell to differentiate into one or more cells or lineages from each of the embryonic germ layer lineages, (i.e. the ectoderm, endoderm and mesoderm).

"Pluripotent," or "pluripotency," refers to the ability of a stem cell to differentiate into one or more cells or lineages from one of the three embryonic germ layer lineages (i.e. the ectoderm, endoderm or mesoderm).

The term "differentiation" as used herein refers to the process of specialization wherein a stern cell, through changes in gene expression, commits to the phenotype of a specific germ lineage (e.g. the ectoderm) and eventually, a specific terminal cell type (e.g. a neuron). A cell may be partially differentiated (e.g. a mesenchymal stem cell) or fully differentiated (e.g. a fibroblast). The adjective "differentiated" is a relative term.

"Migration," or "migrate" as used herein refers to the movement of an endogenous or donor population of cells on, or in, the tissue of an avian embryo. Such migration may occur, for example, from the inside of the compartment, of a brain ventricle, into the surrounding tissue.

"Cell bank" as used herein refers to a stored supply of cells.

"Master cell bank" as used herein refers to a culture of fully characterized cells processed together to ensure uniformity and stability. Cells from a master cell bank are cultured and expanded to provide a working cell bank.

"Working cell bank" as used herein refers to a culture of cells that is derived from a master cell bank.

As used herein, the term "transfection" means the introduction of a nucleic acid, e.g., an expression vector, into a recipient cell by nucleic acid-mediated gene transfer. Transfection may occur in vivo as well as in vitro. One result of transfection is to produce a genetically engineered cell. Cells may be transfected with deoxyribonucleic acid (DNA) and/or ribonucleic acid (RNA).

As used herein, the term "nucleic acid" refers to polynucleotides such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides.

"Immortalized," or "immortalization," as used herein refers to the ability of a genetically engineered (i.e. transformed) cell to reproduce indefinitely.

"Activating agent" as used herein refers to a substance capable of increasing the migration, survival, integration, replication and/or penetration of a stem cell in a host.

"Prenatal" and "fetal" as used herein refer to the period that precedes the birth of a fetus, beginning with the formation of a diploid zygote. Thus, in the context of the invention, tissues and their associated cells derived from a fetus prior to natural birth, or birth by cesarean section, are fetal (i.e. prenatal) tissues. Tissues obtained from mammalian tissue following the birth (e.g. live and still birth) of the mammal are adult tissues and cells derived therefrom are "adult cells." Fetal tissue and fetal cells may be obtained from, for example, miscarried and aborted fetuses.

The term, "clone," or "clonal cell," refers to a single cell which is expanded to produce an isolated population of phenotypically similar cells (i.e. a "clonal cell population").

The term "cell line" refers to one or more generations of cells which are derived from a clonal cell.

DETAILED DESCRIPTION

The invention provides a method for evaluating the neural potency of a cell population in a host environment. In general terms, the invention identifies neuripotency in a cell sample by obtaining a cell sample from, a donor cell population, contacting the cell sample with a developing host avian embryo, and evaluating the ability of cells in the cell sample to assume, a neuripotent phenotype in the host avian embryo environment. The terms "neural potent," "neural potency," "neuripotent," or "neuripotent phenotype" as used herein refers to the ability of a stem cell to differentiate into a cell having a neural cell phenotype such as, for example, a neuron, an astrocyte, or an oligodendrocyte. Cells having a neuripotent phenotype demonstrate the ability to migrate, survive in, differentiate in, pentrate and/or integrate into an avian embryo (e.g. avian brain tissue including ventricles). The invention therefore provides an in vivo means for identifying cells which are capable of assuming a neural phenotype in either an in vitro or in vivo environment.

The ability of the cell sample to assume a neuripotent phenotype may be evaluated, in vivo, using a number of donor cell behavioral characteristics including the donor cells' ability to survive in the host avian embryo. The neuripotent phenotype of a cell sample may also be indicated by the cells' ability to migrate when in contact with the tissues (e.g. brain tissue) of the avian embryo (see e.g. Nature Biotechnology 16, 1033-1039 (1998) Proc. Natl. Acad. Sci. USA Vol. 94, pp. 14809-14814, December 1997). The neuripotent phenotype of cells in the cell sample may also be indicated by the cells' ability to integrate, differentiate in, and penetrate the host avian embryo tissue(s) (see e.g. Stem Cells. February 2006; 24(2):246-57; J Neurosci Methods, Jan. 15, 2006; 150(1); J Neurosci Methods. Jan. 15, 2006; 150(1)).

The invention can be practiced with any type of avian embryo that allows neuripotent cells to assume a neuripotent phenotype. The term "avian" and "avian subjects," as used herein, is intended to include males and females of any avian species, but is primarily intended to encompass poultry which are commercially raised for eggs, meat or as pets. Accordingly, the terms "avian" and "avian subject" encompass chickens, turkeys, ducks, geese, quail, pheasant, parakeets, parrots, cockatoo, cockatiel, ostrich, emu and the like. Chickens and quail are the preferred avian subjects for practicing the invention. Still more preferred avian subjects are chickens. As used herein, "avian embryo" refers to an avian organism from the time of lay (blastodermal stage) through hatching. Thus, the term "avian embryo" as used herein includes stages 1 through 45 under the Hamburger and Hamilton staging model (Series of Embryonic Chicken Growth, J. Morphology, 88 49-92 (1951). An "early embryo" is generally about an embryonic stage 20 (H&H) avian embryo or earlier. The developmental, stages of the chicken embryo are well-understood in the art, see e.g., The Atlas of Chick Development, R. Bellairs & M. Osmond, eds., Academic Press, 1998. In one non-limiting embodiment of the invention, the avian embryo is a stage 26 (H&H) chicken embryo. In another non-limiting embodiment of the invention, the avian embryo is a day 15 ostrich embryo.

In some aspects of the invention, the neural potency of a cell sample is measured by contacting in situ the nervous tissue (e.g. brain tissue) of a developing avian embryo with a cell sample, and observing the migration, integration, survival and/or penetration of the cell, sample in the avian embryo nervous tissue. "Contacting," as used herein, refers to any method that is suitable for placing a cell sample on, in or adjacent to a target tissue, such as the central, nervous tissue of the avian embryo. Such contacting may be accomplished by injection, transplantation, grafting and infusion. In a preferred embodiment, of the invention, the cell sample is introduced to the avian embryo central nervous tissue by injection. As used herein, the terms "injection" and "injecting" encompass methods of inserting a device (typically an elongate device) into an egg or embryo, including methods of delivering or discharging a substance (e.g. cell sample) into an egg or embryo, methods of removing a substance (i.e., a sample) from an egg or embryo, and/or methods of inserting a detector device into an egg or embryo.

The invention may be practiced using any contacting method which allows the cell sample to assume a neuripotent phenotype in the avian embryo. In some aspects of the invention, a cell sample is injected into the avian embryo by making an opening in the shell whereupon a drop of liquid is then placed over the opening in the egg shell such that, the opening is completely covered. The underlying membranes are then cut away, and the cell sample may then be microinjected through the openings in the shell and membranes into the egg, and the opening sealed. Suitable injection methods for practicing the invention are known in the art and include those disclosed in the following references, the contents of which are incorporated herein by reference: U.S. Pat. Nos. 5,897,998 and 7,249,569: and Zeng et al. J. Neurosc. Res. 85:310-320 (2007).

In terms of the central nervous system (CNS) tissue used, the invention may be practiced by contacting the cell sample with any avian embryo CNS tissue (and/or cavity), provided that such tissue (and/or cavity) is capable of supporting the migration, integration, survival, differentiation and/or penetration of cells from a cell sample. One skilled in the art will appreciate that the particular CNS tissue used will depend upon the age of the avian embryo selected for contacting with the cell sample. Suitable CNS tissues for injection of a tissue sample include, but are not limited to, the metencephalon, the mesencephalon, the myelencephalon, the diencephalon, the telencephalon, spinal cord, and combinations thereof. The cell sample may also be injected into one or more cavities of the avian embryo brain including, but not limited to, the lateral ventricle(s), the central canal, the third ventricle, the Rostral portion of the third ventricle, and combinations thereof. In one aspect of the invention, the cell sample is injected into the telencephalon lateral ventricle of, for example, a stage 26 (H&H) chicken embryo.

The invention may be used to evaluate the neural potency of cells having any level of potency. Accordingly, the cell sample may comprise, pluripotent cells, multipotent cells, lineage-committed precursor cells, and combinations thereof.

In a preferred embodiment, the invention is used to evaluate the neural potency of a cell sample that is derived from a mammalian donor source. Such cell samples may be derived from any mammalian donor source that is capable of being evaluated for neural, potency when contacted with an avian embryo as disclosed herein. Suitable donor mammals for deriving cell samples include, but are not limited to, human, primate, dog, cat, sheep, rabbit, pig, bovine, horse, rat, mouse and combinations thereof. In a preferred embodiment the cell sample is derived from a human tissue source.

Cell samples for use with the invention may be derived from any mammalian tissue provided that the cells obtained therefrom are capable of being evaluated for neural potency according to the methods disclosed herein. Accordingly, cell samples may be derived from adult mammalian tissue sources, fetal mammalian tissue sources, and combinations thereof. Fetal mammalian tissues may be obtained through, for example, the abortion or miscarriage of a fetus. Cell samples for use with the invention may also be derived from adult tissue sources including, but not limited to, cadaver donor sources, live donor sources, and combinations thereof.

The method of the invention can be used to evaluate the potency of cell samples derived from any type of tissue. Accordingly, cell samples may be derived from central nervous tissue (e.g. the brain, brain stem and/or spinal cord), bone marrow, peripheral blood, placenta, umbilical cord blood, ocular tissues, umbilical cord, placenta, amniotic fluid, and combinations thereof. In preferred embodiments, the cell samples are derived from brain tissue. In still more preferred embodiments, the cell samples are derived from the brain tissue of a human aborted fetus at seven to 12 weeks of gestation.

Cells samples for use with the invention may be derived from cell sources having varying levels of purity. Accordingly, cells samples may be derived from a primary tissue culture, a clonal cell line (i.e. master banked cell line), cells selectively expanded from a primary tissue culture, or a combination thereof. As used herein, the term "purified," or "isolated," means that a cell population has been separated from its natural environment (i.e. the body) and that at least 50% of the cells in the cell population share a common genotype and phenotye, A clonal cell population, which is essentially, free of other cells, is one non-limiting example of a purified cell sample.

In some embodiments, the invention is used to evaluate the neural potency of mesenchymal stem cells or progenitor cells. Mesenchymal stem cells for use with the invention may be derived from any mesenchymal stent cell source that can provide cells capable of being evaluated for neural potency according to the methods disclosed herein. Some suitable mesenchymal cell sources include, but are not limited to, umbilical cord blood, placenta, Wharton's jelly, bone marrow, chorionic villus, adipose tissue, menstrual discharge, amniotic fluid and peripheral blood, dermis, or a combination thereof.

The invention also contemplates evaluating the neural potency of cell samples which are derived from embryonic stem cells. This includes cell samples comprising pluripotent embryonic stem cells, cells which have been differentiated from embryonic stem cells, and combinations thereof.

Once a cell sample source is decided upon, the cell sample is prepared for contacting with an avian embryo. One skilled in the art will appreciate that the method that is used for preparing the cell sample will depend upon the donor source of the cell sample and the manner in which the cell sample is to be contacted with the avian embryo, in a preferred embodiment, the cell sample is prepared for contacting with the avian embryo as an injection. In general terms, the cell sample is prepared for injection by suspending the sample cell population in a suitable pharmaceutical carrier. Pharmaceutical carriers for use with the invention include, but are not limited to, saline, phosphate buffered saline, trypan blue and Culture media. Some other non-limiting examples of pharmaceutically acceptable carriers include, hut are not limited to, those listed in Remington's Pharmaceutical Science (18.sup.th Ed., ed. Gennaro, Mack Publishing Co., Easton, Pa., 1990) and the Handbook of Pharmaceutical Excipients (4.sup.th ed., Ed. Rowe et al. Pharmaceutical Press, Washington, D.C.), each of which is incorporated by reference. Methods for preparing the cell sample for injection are known in the art as taught by the following references, the disclosures of which are incorporated herein by reference: Methods In Molec. Biol. (2006) 331:137-142; and Develop. Dynam. (2005) 233:496-515.

Although any suitable, method for preparing the cell sample for injection may be used, the precise method for preparing the cell, sample may vary according to the source from which the cell sample is obtained. For example, if the cell sample is obtained from a tissue (e.g. brain tissue), the tissue may be made into a suspension by cutting the tissue into pieces, followed by enzymatic digestion and trituration such as by gentle pipetting. The cells may then be separated by centrifugation and/or filtration. If the cell sample is obtained from a cell culture (e.g. primary culture or cultured cell line), the cells may be prepared for injection by gentle pipetting, and if necessary, enzymatic digestion, it is also contemplated that the cell sample may assume the form of a whole tissue which is contacted with the avian embryo. For example, contacting the avian embryo with the cell sample may be accomplished by transplanting a small piece of tissue (e.g. brain tissue) to the avian embryo.

In some aspects of the invention, the cell sample is treated with one or more agents prior to the cell sample being contacted with, the avian embryo. Agents for treating (i.e. contacting) the cell sample before the cell sample is contacted with the avian embryo include priming agents, activation agents and combinations thereof. "Priming agent," or "differentiation agent," as used herein refers to one of a collection of compounds that are used in culture systems of this invention to produce differentiated cells of the neural lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others, or acting in concert with other agents through unknown mechanisms.

Suitable differentiation agents for use with the invention include, for example, retinoic acid, fetal or mature neuronal cells including mesencephalic or striatal cells or a growth factor or cytokine such as brain derived neurotrophic factor (BDNF), glial derived neurotrophic factor (GDNF), nerve growth factor (NGF) growth factors [e.g. fibroblast growth factor (FGF), transforming growth factors (TGF)], ciliary neurotrophic factor (CNTF), bone-morphogenetic proteins (BMP), leukemia inhibitory factor (LIF), gial fibrillary acidic protein (GFAP), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, thrombopoietin, silencers, (including glial-cell missing, neuron restrictive silencer factor), antioxidants such as vitamin-E (tocopherol) and vitamin E esters, among others including lipoic acid. SHC (SRC-homology-2-domain-Containing transforming protein), neuroproteins, proteoglycans, glycoproteins, neural adhesion molecules, other cell-signalling molecules and combinations thereof.

The cell sample may contain any number or concentration of cells that allows the cell sample to be evaluated for neural potency when contacted with an avian embryo as disclosed herein. One skilled in the art will appreciate that the number of cells injected will depend upon the size (i.e. age and type) of the avian embryo, and the particular location where cell, sample is to be injected. The cell sample may contain any functional range of cell numbers. In one embodiment, for example, the cell sample comprises between about $2\times10^5$ and $4\text{-}6\times10^5$ cells. In a more limited embodiment of the invention, the cell sample comprises about $2\times10^5$ cells (e.g. neural stem cells) which are injected into the telencephalon lateral ventricle of a chicken embryo at stage 26 (H&H). In another embodiment, $4\text{-}6\times10^5$ cells (e.g. neural stem cells) are injected into the neural tissue of an ostrich embryo at day 10.

By contacting the cell sample (of donor cells) with the avian embryo, a chimeric avian embryo is produced. As used herein, the phrase "chimeric avian embryo" refers to an avian embryo that is in contact with cells that have a different genotype than the avian embryo. Thus, for example, the donor cell sample may be derived from a different species (e.g. a mammalian species) than that of the avian embryo. By "different genotype," it is also meant that the genotype of the cell sample may comprise recombinant cells which have been, modified with an exogenous nucleic acid.

After the cell sample is contacted with, the avian embryo, the incubation and development of the resulting chimeric avian embryo is continued for a suitable reaction time to allow the cells in the cell sample to express a neuripotent phenotype. As used herein, the phrase "reaction time" refers to the period of time that it takes for a neuripotent cell sample to express a neuripotent phenotype in a chimeric avian embryo. Thus, the incubation conditions for the chimeric avian embryo are maintained for a time that is sufficient to allow the cells in the cell sample to migrate, penetrate, survive in, differentiate in or integrate in the avian embryo tissue. Suitable reaction times may vary with the type of avian embryo, as well as the age of the avian embryo at the time of injection. For example, in embodiments where the avian embryo is a chicken embryo, the cell, sample may be provided with a reaction time of between about 4 and 6 days. In one aspect of the invention, a cell sample is contacted with a chicken embryo at stage 26 (H&H), and evaluated for its neural potency after a reaction time of 4 days (i.e. when the chicken embryo is at stage 36). In another aspect of the invention, a cell sample is contacted with a chicken embryo at stage 26 (H&H), and evaluated for its neural potency after a reaction time of 6 days (i.e. when the chicken embryo is at stage 38). Although specific reaction times are disclosed here, one skilled in the art will appreciate that the invention may be practiced with any reaction time that allows a cell sample to be evaluated for its neuripotency when contacted with an avian embryo as disclosed herein.

Neuripotency of the cell sample may be measured according to any means which provides an indication that the cell sample comprises cells capable of assuming a neural phenotype. For example, the neuripotency of the cell sample may be evaluated by monitoring one or more neuripotency markers including, but not limited to, cell migration, differentiation, cell survival, and cell integration/penetration into the host tissue (see e.g. Spine. Sep. 15, 2004; 29(18): 1971-9; J Neurocytol May 2004; 33(3):309-19; Exp Neurol. January 2007; 203(1): 128-36. Epub Sep. 29, 2006; Proc Natl Acad Sci USA. Dec. 28, 2004; 101(52): 18117-22. Epub Dec. 17, 2004; Proc Natl Acad Sci USA. Nov. 7, 2000; 97(23): 12846-51).

Cell migration, differentiation, survival and integration/penetration (i.e. neuripotency markers) may be monitored using a variety of techniques which are available in the art. In one aspect of the invention the cells from the cell sample are labeled with a dye (e.g. a lipid-based fluorescent dye such as DiI and DiO, carboxyfluorescein-diacetate-succinyl-ester), gold particles, Bromodeoxyuridine (BrdU), quantum dot or any other label known in the art that may be detected after delivery of the cells to the recipient embryo. Alternatively, the donor cells may carry particular epitopes or reporter genes that may be detected using antibodies or standard nucleic acid detection methods to identify the presence and location of cells from the cell sample. "Reporter genes" are those genes that "report" the presence of particular cell's. Reporter genes' may be introduced into cells by transfection. Suitable reporter genes for use with the invention include, but are not limited to fluorescent protein, Lac Z, firefly Rennila protein, red, yellow or blue cyan fluoresce.

In one aspect of the invention, the migration, differentiation survival and integration/penetration of the cell sample is evaluated using immunohistochemical analysis. For example, after contacting the avian embryo with a cell sample, the resulting chimeric avian embryo may be cut into tissue sections and the movement of the cell sample resolved using immunohistochemical staining. Staining may be accomplished using, for example, antibodies labeled with any suitable marker including, but not limited to, fluorescent markers (e.g. fluorescein or rhodamine), an enzyme that supports a color producing reaction with a substrate (e.g. horseradish peroxidase or alkaline phosphatase), ferritin or other electron dense particles, and radiolabels (e.g. $I^{125}$). Antibodies for carrying out histochemical analysis may be monoclonal or polyclonal.

Tissue sections and cell suspensions are prepared for immunohistochemical examination according to common histological techniques. After the avian embryo is contacted with the cell sample, the cells in the cell sample are given an opportunity to migrate through the avian tissue. The particular amount of time that is required will depend upon the age of the avian embryo as well as the particular avian tissue that is contacted with the cell sample. In one aspect, of the invention, a stage 26 chicken embryo is prepared for immunohistochemical examination 6 days after the cell sample is contacted with the avian embryo. The relative amount of migration, survival and integration/penetration of a cell sample may be obtained by comparing these parameters at different times after the avian embryo is contacted with the cell sample. For example, the avian embryo tissue that is contacted with the cell sample may be analyzed for cell sample migration shortly after contacting (e.g. minutes or hours after injection of the cell sample) and again, several days after contacting. The relative amount of migration between the timepoints may then be compared to provide a relative value of neural potency with greater distances of migration indicating greater neural potency.

The neural potency of a cell sample may also be compared to negative and positive control cell samples. For example, a cell sample may be evaluated for migration, survival and integration/penetration relative to a cell sample that is completely lacking in neural potency. Similarly, the migration, survival and integration/penetration of a cell sample may be compared to a cell sample of known neural potency (e.g. a neuronal progenitor cell population).

The method of the invention lends itself to any application where identifying the neural potency of a population of cells is desired. For example, the invention may be used for the screening of cell candidates for establishing a master cell bank of neuripotent stem cells. In such applications, a cell sample is obtained from a population of cells and evaluated for its neural potency according to the methods disclosed herein. If the cell sample tests positive for neural potency, the population of cells from which the sample was obtained can be expanded and preserved as a master cell bank. The invention therefore provides an efficient means for avoiding the isolation, expansion and preservation of cell lines which lack neuripotency.

In another aspect, the invention is used as a means for the validation of a cell bank of neuripotent cells. In other words, the invention provides a means for confirming that a cell bank (e.g. a master cell bank or working cell bank) of cells known to be neuripotent has retained its neuripotency. Thus, without being limited to any particular theory, the invention identifies working cell banks which may have a diminished neuripotency due to factors such as cryopreservation, culture conditions, contamination and/or expansion. In such embodiments, a sample from a bank of cells known to be neuripotent is contacted with an avian embryo as disclosed herein. The observation of a neuripotent phenotype in the avian embryo then provides an indication (i.e. verifies) that the cell bank of known neuripotent cells has retained its neuripotency.

In another aspect, the invention provides a screening assay for selecting candidate cell lines for further study in the treatment of a neurological disorder. In one aspect, this embodiment of the invention involves screening a plurality of different donor cell populations for their potential as a cell therapy for a neurological disorder. Cell samples are obtained for each of the different donor cell populations and contacted with an avian embryo as disclosed herein. Those donor cell populations that demonstrate neuripotency (i.e. migration, differentiation, survival, integration/penetration) may then be identified as potential cell populations for the treatment of a neurological disorder such as, for example, ischemic stroke, Alzheimer's disease or Parkinson's disease. Similarly, the invention may be used to evaluate combinations of donor cell types as a potential therapy for treating a neurological disorder. For example, a combination of cells from different donor cell populations may be evaluated for neuripotency by contacting the combination of cells (as a cell sample) with an avian embryo as disclosed herein. Those combinations of donor cells that demonstrate diffentiation, migration, survival, and/or penetration/integration may then be identified as a candidate combination therapy for treating a neurological disorder.

In another aspect, the invention finds use in identifying priming agents, or combinations of priming agents, that are capable of enhancing the neural differentiation of a cell population. These embodiments involve selecting a cell sample from a known neuripotent cell population and contacting the cell sample with at least one candidate priming agent. The cell sample is then is contacted with the avian embryo as disclosed herein. The effects of the candidate priming agent(s) on the neuripotency of the cell sample may then be evaluated by observing the migration, differentiation, survival, and penetration/integration of the cell sample as disclosed above. Those candidate priming agents that increase or support the migration, survival, and penetration/integration of the cell sample may then be identified as priming agents that that are capable of inducing neural differentiation in a cell population.

Similarly, the invention may be used to identify those combinations of priming agents that are capable of promoting neural differentiation. In a similar fashion, the method of the invention lends itself to identifying the optimum concentration of priming agents for inducing differentiation. In general terms, this is done by contacting a cell sample with a selected concentration of a priming agent, contacting an avian embryo with the cell sample, and then evaluating the ability of the priming agent concentration to induce migration, survival, and penetration/integration. The concentration of priming agent that provides the greatest migration, differentiation, survival, and penetration/integration of the cell sample may then be identified as the optimum concentration for that priming agent.

Incubation times for using a priming agent to achieve a desired level of neuripotency in a cell population may vary with a number of conditions including, the cell population's cell passage number, donor source (e.g. mesenchymal vs. ectodermal cell lineages), culture methods use to expand the cell population, cell population genotype, and the like. Thus, the invention may be used to identify a incubation time for achieiving a desired level of neuripotency in a given cell population using a particular priming agent (or combination of priming agents). This may be done by following the steps of (a) selecting a population of cells, (b) selecting a priming agent (or combination of priming agents), (c) contacting the population of cells with the priming agent (or combination of priming agents) for a selected incubation period, (d) contacting the population of cells from step (c) with an avian embryo, and (e) identifying the ability of the selected incubation period to induce the population of cells to assume a desired level of neuripotentcy in the avian embryo.

In another aspect, the invention provides a screening assay for identifying a candidate therapy for a treating neurological disorder, wherein the candidate therapy comprises cells and an agent selected from priming agent(s), activation agent(s) and combinations thereof. These embodiments involve selecting a cell sample and selecting a priming agent(s) and/or an activation agent, and contacting the cell sample with the selected priming agent(s) and/or an activation, agent. The combination of the cell sample, priming agent, and/or activation agent is then contacted by an avian embryo as disclosed herein. Those combinations of cells, priming and/or activation agents that increase or support the migration, differentiation, survival, and penetration/integration of the cell sample may then be identified as a candidate therapy for a treating neurological disorder.

In another aspect, the invention provides a means for identifying the optimal number of passages for obtaining a neuripotent cell population. That is, the method can be used to identify that number of passages that allows a transplanted cell population the greatest ability to assume a neuripotent neural phenotype in vivo or in vitro. In general terms, this is accomplished by: (a) culturing a cell population for a first number of passages; (b) obtaining a first cell sample from said cell population, after said first number of passages; (c) culturing said cell population for a second number of passages; (d) obtaining a second cell sample from said cell population after said second number of passages; (e) contacting said first cell sample with a first avian embryo and contacting said second cell sample with a second avian embryo; (f) comparing the migration, differentiation, survival, and/or integration/penetration of said first cell sample and said second cell sample; (g) identifying the cell sample having the greatest amount of migration, survival, and/or integration/penetration as the cell sample having the optimal number of cell passages.

In another aspect of the invention, a means for optimizing cell culture conditions for obtaining a neuripotent cell population is provided. These embodiments generally involve subjecting a number of cell populations (i.e. donor cell samples) to different cell culture conditions. The different cell samples are then contacted with an avian embryo and evaluated for their ability to assume a neuripotent phenotype as disclosed herein. Those cell culture conditions which provide cell samples expressing a neuripotent phenotype in the avian embryo host may then be identified as a culture condition for obtaining a neuripotent cell population. Thus, the invention may provide a means for applying neuripotent cell culture conditions for the production of a larger population of neuripotent stem cells. The method, of the invention may be used to evaluate a number of cell culture conditions including, but not limited to, the collection, expansion, priming, and/or activation of a population of donor cells. The ability of a given cell culture condition to produce a neuripotent cell population may be evaluated using cells of known neuripotency, or cells whose neuripotency is unknown.

In another aspect of the invention, a means for screening for neural differentiation agents is provided. In such embodiments, a cell sample from a population of donor cells known to have a neuripotent phenotype is contacted with a candidate differentiation agent. The cell sample is then contacted with an avian embryo and evaluated for the cell sample's ability to assume a neuripotent phenotype as disclosed herein. Those candidate differentiation agents that increase the ability of the cell, sample to assume a neuripotent phenotype (relative to a cell sample of identical cells that was not treated with a candidate differentiation agent) in the avian embryo may then be identified as an agent capable of inducing the differentiation of a neuripotent cell population.

EXAMPLE 1

Neural Stent Cells and Cultures

The purpose of this experiment was to observe the in vivo migration of a cell sample of human neural cells using a chicken embryo.

Human neural stem cells were collected from 13 week-old fetal brain. Brain tissue was freshly dissected and dissociated in Accutase (Sigma Aldrich) for 30 min at 37° C. The cells were seeded in serum-free neural basal medium in 100 mm cell culture dish. Neurobasal medium was used for basal medium to maintain NSCs in an undifferentiated condition. The components included: Neurobasal (96%; Gibco/Invitrogen, Grand Island, N.Y.); GlutaMAX (1%; Gibco/Invitrogen); Heparin (8 mg/ml: Sigma-Aldrich, St. Louis, Mo.) (26). To this added the following factors were added: basic Fibroblast Growth Factor and Epidermal growth factor (bFGF; 20 ng/ml; EGF; 20 ng/ml; human, recombinant; Chemicon International, Temecula, Calif.) and Leukemia Inhibitory Factor (LIF; 10 ng/ml; human, recombinant; Chemicon International). For routine passaging, TrypLE was used as the dissociating agent (Invitrogen).

NSCs were differentiated in 2% fetal bovine serum neurobasal medium without growth factors (bFGF, EGF, and LIF) for 10 days. NSCs were seeded in laminin coated dish with another differentiation medium contains 2% fetal bovine serum neurobasal medium with heparin (8 mg/ml; Sigma-Aldrich, St. Louis, Mo.), bFGF; 10 ng/ml (Chemicon International, Temecula, Calif.), N2 supplement (1%, Gibco/Invitrogen), laminin (1 μg/ml, Sigma-Aldrich, St. Louis, N.Y.).

EXAMPLE 2

Chicken Embryos and NSC Translation

Pathogen-free fertilized chicken embryos were obtained from SPEFAS (North franklin, Conn.) and staged according to Hamburger and Hamilton (H&H) (1951).

NSCs were subcultured 72 hr prior to transplantation. Undifferentiated NSCs and differentiated NSCs were collected and a cell sample; of $2\times10^5$ cells was prepared for each of the differentiated NSCs and undifferentiated NSCs. The cell samples were injected, i.e. transplanted into telencephalon lateral ventricle of chicken embryos at H&H stage 26. Transplanted chicken embryos were incubated at 37° C. for 6 days. Chicken embryo brains were collected and embedded with OCT Cryo Tech for cryosection.

EXAMPLE 3

Immunohistochemistry

Cryosection slides were placed at room temperature for 30 min. Slides were fixed by pre-cooled acetone for 5-10 min at room temperature and treated with 0.3% $H_2O_2$ in 100% methanol for 10 min to quench endogenous peroxidase activity. Slides were washed 3 times with PBS for 5 min each. Chicken brains were incubated with anti-human nestin (1:3000, chemicon international Inc.) and nuclei (1:500, Chemicon International Inc.) for one hour at room temperature. Slides were washed in PBS 3 times, 5 min for each, and exposed to secondary antibodies Alexa fluor 488-conjugated goat anti-mouse IgG (1:400) and Alexa Fluro 647-conjugated goat anti-rabbit IgG (1:400) for 30 min at room temperature. Slides were washed with PBS 3 times, 5 min each, and counterstained with DAPI for 10 min at room temperature. Slides were washed in PBS 3 times, 5 min for each, and mounted with immunofluorescence mounting media from Sigma-Aldrich.

Results

Figure 2:
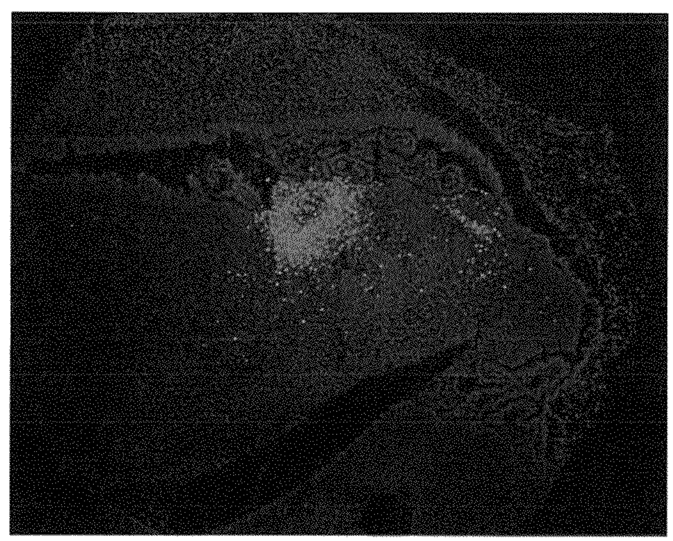
FIG. 2 depicts thin sections of the lateral ventricle of a stage 38 (H&H) chicken embryo brain at 4× magnification after the chicken embryo was injected with undifferentiated human neural stem cells at Stage 26 (H&H) (i.e. six days after injection). Human neural stem cells were detected by human specific nuclei antibody.
Figure 3:
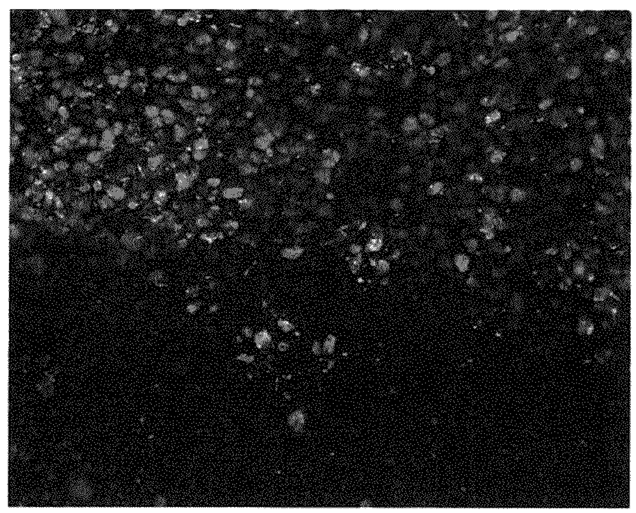
FIG. 3 depicts the image of FIG. 2 at 40× magnification. Human specific nuclei and nestin antibodies were used to detect transplanted human cells in chicken embryo brain at stage 38 (H&H).
Figure 4:
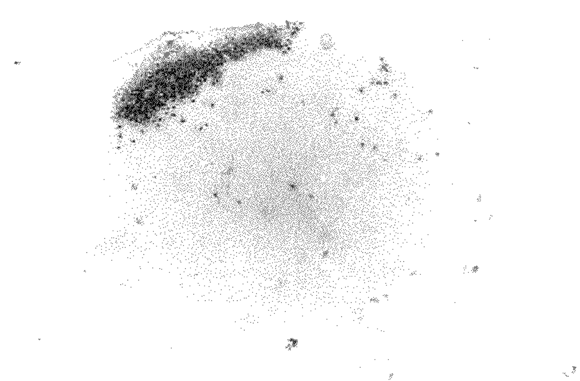
FIGS. 4-7 depict thin sections of the lateral ventricle of a stage 38 (H&H) chicken embryo brain at 4× magnification after the chicken embryo was injected with undifferentiated neural stem cells at Stage 26 (H&H).
Figures 5, 6:
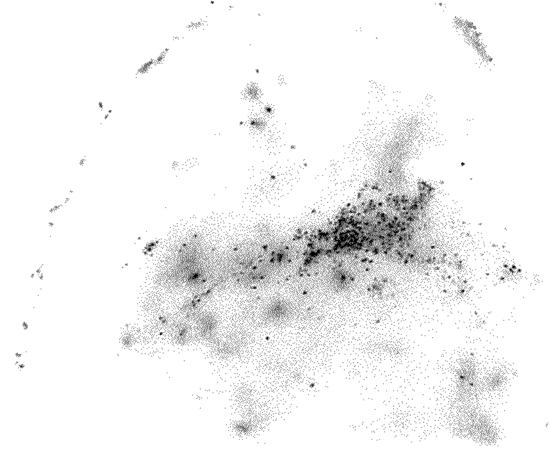
Figures 7, 8:
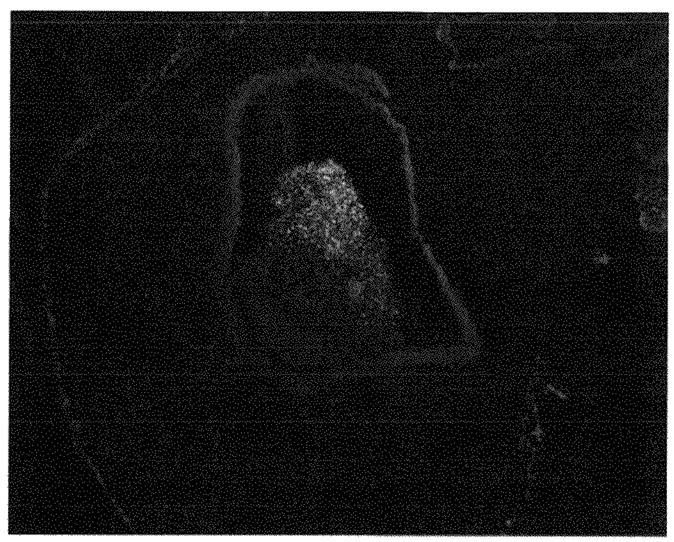
FIG. 8 depicts thin sections of the lateral ventricle of a stage 38 (H&H) chicken embryo brain at 4× magnification after the chicken embryo was injected with differentiated neural stem cells at Stage 26 (H&H). Human specific nuclei and nestin antibodies were used to detect transplanted human cells in the chicken embryo brain. Data showed that there was no migration of differentiated human neural stem cells in the chicken embryo brain. Differentiated human neural stem cells stayed in the lateral ventricle of the chicken embryo forebrain.
Figure 9:
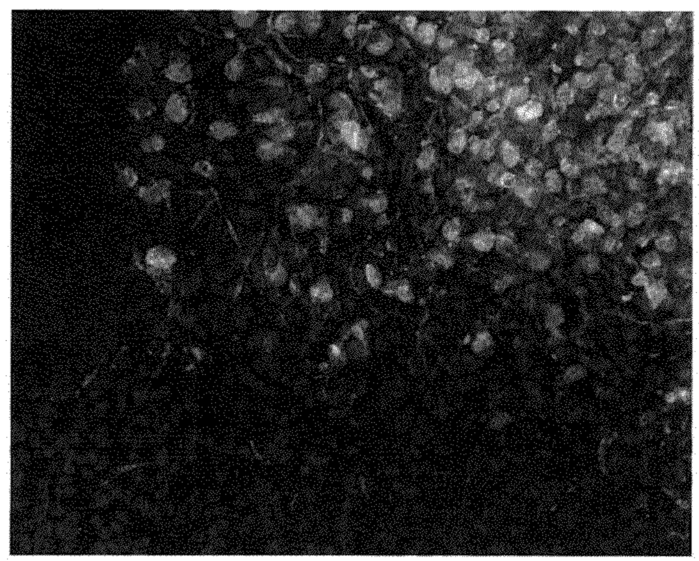
FIG. 9 depicts the image of FIG. 8 at 100× magnification. Human specific nuclei and nestin antibodies were used to detect transplanted human cells in chicken brain at stage 38 (H&H).
Figure 10:
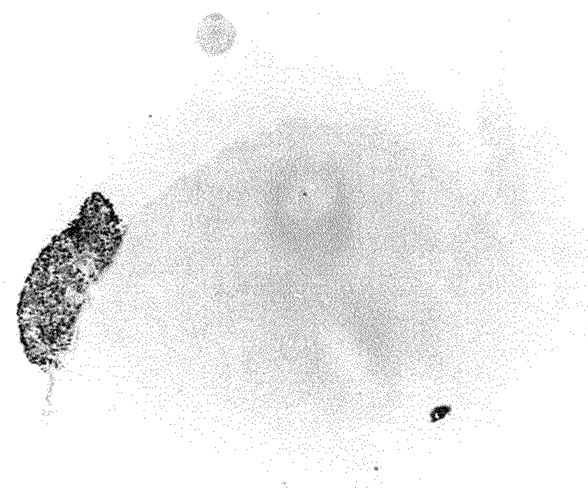
FIGS. 10-12 depict thin sections of the lateral ventricle of a stage 38 (H&H) chicken embryo brain at 4× magnification after the chicken embryo was injected with differentiated neural stem cells at Stage 26 (H&H).
Figures 11, 12:
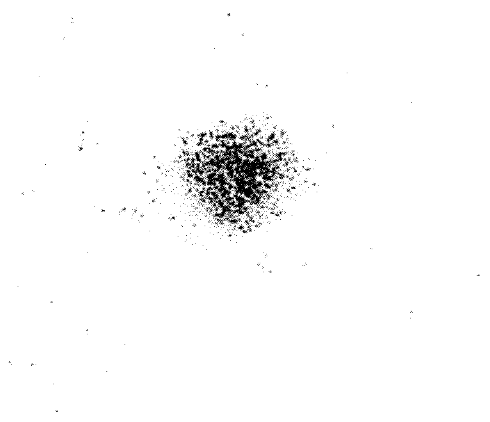

The differentiated and undifferentiated NSCs from Example 1 above were used to test the chicken embryo model. Human specific nuclei and nestin were used to detect human cells after transplantation. Undifferentiated NSCs were observed to migrate into brain primordia through ventricle zone at stage 38 (FIGS. 2-7). Cell migration was therefore observed at least four days after transplantation. The distance of migration was time-dependent (data not shown). Migrating cells expressed neural precursor marker, nestin which suggested transplanted cells retained their potency. However, only few migrated cells were detected in differentiated human neural stem cells six days after transplantation (FIGS. 8-12). Most of the differentiated NSCs stayed in the lateral ventricle of the chicken embryo forebrain (FIGS. 8-12). Interestingly, differentiated human neural stem cells still expressed nestin but did not migrate into brain striatum. The results are summarized in Table 1 below.

Different markers are often used for identifying neural stem cells. Our data showed that undifferentiated and differentiated neural stem cells expressed precursor marker, nestin six days after transplantation. They showed, however, different biological functions six days after transplantation in chicken embryo brains which suggested our chicken embryo model provides a useful assay for verifying biological function of stem cell potency.

TABLE 1

| Cell types | Migration and Engraftment |
|---|---|
| Unifferentiated Neural stem cell sample A | +++ |
| Undiffferentiated Neural stem cell sample B | +++ |
| Undiffferentiated Neural stem cell sample C | +++ |
| Differentiated neural stem cell sample A | +/−− |
| Differentiated neural stem cell sample B | +/−− |
| Differentiated neural stem cell sample C | +/−− |

This experiment established the invention as a reliable assay or screening method for verifying and testing stem cell potency. The assay tested the capability of donor NSCs to penetrate, migrate, survive, differentiate and integrate in vivo in a host avian embryonic brain. The method of the invention finds utililty for testing the potency effects of various conditions of priming and activation, and combinations of priming and activation conditions.

The methods of the invention Include potency evaluation of master cell banks during stem cell manufacturing; and evaluation of working cell banks derived from said master cell banks.

We claim:

1. A method for identifying a neuripotent cell population comprising:

(a) obtaining a cell sample from a population of donor cells;

(b) contacting an intact ventricle in the neural tissue of an avian embryo with said cell sample; and (c) identifying that at least a portion of cells in said ceil sample demonstrate a neuripotent phenotype after contacting the intact ventricle in the neural tissue of said avian embryo.

2. The method of claim 1, wherein said neuripotent phenotype is selected from at least one of migration, integration, survival and penetration.

3. The method of claim 1, wherein said population of donor cells comprises mammalian cells.

4. The method of claim 3, wherein said mammalian cells are human cells.

5. The method of claim 4, wherein said human cells are neural cells.

6. The method of claim 5, wherein said neural cells are obtained from fetal tissue.

7. The method of claim 3, wherein said mammalian cells are neural cells.

8. The method of claim 1, wherein said avian embryo comprises a chicken embryo.

9. The method of claim 1, wherein said intact ventricle is a lateral ventricle.

10. The method of claim 9, wherein said lateral ventricle is in the telencephalon of said avian embryo.

11. The method of claim 1, wherein said population of donor cells is free of immortalized cells.

12. The method of claim 1, further comprising banking the population of donor cells.

13. The method of claim 12, wherein said banking comprises masterbanking.

14. The method of claim 1, wherein said method is used to confirm the neuripotency of a masterbank of neuripotent cells.

15. The method of claim 1, wherein said method is used to confirm the neuripotency of a working bank of neuripotent cells.

16. The method of claim 1, wherein said ventricle is in the brain of said avian embryo.

17. A method for measuring the activity of a neuripotent cell population comprising:

(a) obtaining a cell sample from said neuripotent cell population;

(b) contacting an intact ventricle in the neural tissue of an avian embryo with said cell sample;

(c) measuring the activity of said cell sample based on the ability of said cell sample to migrate, survive, integrate and/or penetrate said avian embryo.

18. The method of claim 17, wherein said cell sample is treated with an activating agent.

19. The method of claim 17, wherein said intact ventricle is a lateral ventricle.

20. The method of claim 17, wherein said intact ventricle comprises germinal epithelium.

21. The method of claim 1, wherein said intact ventricle comprises germinal epithelium.

22. The method of claim 17, wherein said intact ventricle is a lateral ventricle in the telencephalon of said avian embryo.

23. A method for identifying a population of cells having a neural stem cell phenotype, said method comprising:

(a) providing a population of cells;

(b) providing an avian embryo comprising neural tissue having one or more intact ventricles;

(c) contacting said one or more intact ventricles with said population of cells; and (d) observing at least one of migration, integration, survival and penetration by at least a portion of the contacted cells in said one or more intact ventricles;

(e) wherein said observing identities said population of cells as having a neural stem cell phenotype.

24. The method of claim 23, wherein said population of cells comprises mammalian cells.

25. The method of claim 24, wherein said mammalian cells are human cells.

26. The method of claim 25, wherein said human cells are neural cells.

27. The method of claim 24, wherein said mammalian cells are neural cells.

28. The method of claim 23, wherein said avian embryo is a chicken embryo.

29. The method of claim 23, wherein contacting comprises contacting said population of cells with an intact lateral ventricle.

30. The method of claim 23, wherein said population of cells is obtained from a donor source selected from at least one of tissue, cultured cells, a clonal cell line, and a primary culture of cells.

31. The method of claim 30, further comprising creating a masterbank of cells from said donor source.

32. The method of claim 31, wherein said donor source comprises neural tissue.

33. The method of claim 23, wherein said population of cells is obtained from a masterbank of neural stem cells.

34. The method of claim 23, wherein said population of cells is obtained from a working bank of neural stem cells.

35. The method of claim 23, wherein contacting comprises contacting said population of cells with the germinal epithelium of said one or more intact ventricles.

36. The method of claim 23, wherein said one or more intact ventricles are in the brain of said avian embryo.

37. A method for identifying a donor source for producing a masterbank of neural stem cells, said method comprising:

(a) providing a cell sample from a donor source;

(b) providing an avian embryo;

(c) contacting at least one intact ventricle in the brain of said avian embryo with said cell sample;

(d) observing in said at least one intact ventricle at least one of migration, integration, survival and penetration by at least a portion of the cells in said cell sample, wherein said observing identifies said donor source as a source of neural stem cells; and (e) producing a masterbank of cells from said donor source.

38. The method of claim 37, wherein said at least one ventricle is in at least one of the metencephalon, mesencephalon, myelencephalon, diencephalon or telenchephalon of said brain of said avian embryo.

39. The method of claim 38, wherein said at least one ventricle is a lateral ventricle in the telencephalon of said avian embryo.

* * * * *